United States Patent
Pertzov et al.

(10) Patent No.: US 11,020,034 B2
(45) Date of Patent: Jun. 1, 2021

(54) CONCEALED INFORMATION TESTING USING GAZE DYNAMICS

(71) Applicant: YISSUM RESEARCH DEVELOPMENT COMPANY OF THE HEBREW UNIVERSITY OF JERUSALEM LTD., Jerusalem (IL)

(72) Inventors: Yoni Pertzov, Tel Aviv (IL); Gershon Ben Shakhar, Jerusalem (IL)

(73) Assignee: YISSUM RESEARCH DEVELOPMENTCOMPANY, Jerusalem (IL)

( * ) Notice: Subject to any disclaimer, the term of this patent is extended or adjusted under 35 U.S.C. 154(b) by 0 days.

(21) Appl. No.: 16/612,420

(22) PCT Filed: May 10, 2018

(86) PCT No.: PCT/IL2018/050514
§ 371 (c)(1),
(2) Date: Nov. 11, 2019

(87) PCT Pub. No.: WO2018/207190
PCT Pub. Date: Nov. 15, 2018

(65) Prior Publication Data
US 2020/0281515 A1    Sep. 10, 2020

Related U.S. Application Data

(60) Provisional application No. 62/641,595, filed on Mar. 12, 2018, provisional application No. 62/504,253, filed on May 10, 2017.

(51) Int. Cl.
*A61B 5/16*    (2006.01)
*G06F 3/01*    (2006.01)

(52) U.S. Cl.
CPC .............. *A61B 5/163* (2017.08); *G06F 3/013* (2013.01)

(58) Field of Classification Search
CPC ......... A61B 5/163; A61B 5/164; G06F 3/013; G06F 21/36; G06F 3/038; G06F 21/316
See application file for complete search history.

(56) References Cited

U.S. PATENT DOCUMENTS

| | | | |
|---|---|---|---|
| 2011/0043759 A1 | 2/2011 | Bushinsky | |
| 2013/0090562 A1* | 4/2013 | Ryan | ...................... A61B 5/165 600/473 |
| 2017/0119295 A1* | 5/2017 | Twyman | ............... A61B 5/4884 |

FOREIGN PATENT DOCUMENTS

| | | | |
|---|---|---|---|
| WO | 2011/049558 A1 | 4/2011 | |
| WO | WO-2011049558 A1 * | 4/2011 | ............. A61B 5/164 |

OTHER PUBLICATIONS

PCT Search Report and Written Opinion for International Application No. PCT/IL2018/050514 dated Aug. 27, 2018, 12 pp.
(Continued)

*Primary Examiner* — Joseph W Becker
(74) *Attorney, Agent, or Firm* — The Roy Gross Law Firm, LI; Roy Gross

(57) ABSTRACT

An eye tracking-based concealed information testing, which includes: presenting images of objects at certain coordinates on a computer display; operating a camera to track eye movements of a human subject observing the display; computing one or more gaze parameters for each of the objects, based on the tracked eye movements and the certain coordinates; and determining that a certain one of the objects is familiar to the human subject based on the gaze parameter. The eye tracking-based concealed information testing is optionally integrated with a short-term memory task, to enhance detection of concealed information.

17 Claims, 7 Drawing Sheets

(56) References Cited

OTHER PUBLICATIONS

PCT Preliminary Report on Patentability for International Application No. PCT/IL2018/050514 dated Nov. 12, 2019, 9 pp.
Althoff, R. R., & Cohen, N. J. (1999). Eye-movement-based memory effect: a reprocessing effect in face perception. Journal of Experimental Psychology: Learning, Memory, and Cognition, 25(4), 997.
Arizpe, J., Kravitz, D. J., Yovel, G., & Baker, C. I. (2012). Start position strongly influences fixation patterns during face processing: Difficulties with eye movements as a measure of information use. PloS One, 7(2), e31106.
Baddeley, A. (2000). The episodic buffer: a new component of working memory? Trends in Cognitive Sciences, 4(11), 417-423.
Benjamini, Y., & Hochberg, Y. (1995). Controlling the false discovery rate: a practical and powerful approach to multiple testing. Journal of the Royal Statistical Society. Series B (Methodological), 289-300.
Ben-Shakhar, G. (1977). A further study of the dichotomization theory in detection of information. Psychophysiology, 14(4), 408-413.
Ben-Shakhar, G. (2011). Countermeasures. In: B. Verschuere, G. Ben-Shakhar, & E. Meijer, E. Memory detection: theory and application of the Concealed Information Test. Cambridge University Press, 200-215.
Ben-Shakhar, G., Lieblich, I., & Kugelmass, S. (1970). Guilty knowledge technique: Application of signal detection measures. Journal of Applied Psychology, 54(5), 409.
Cowan, N. (2001). Metatheory of storage capacity limits. Behavioral and Brain Sciences, 24(01), 154-176.
Devue, C., Van der Stigchel, S., Brédart, S., & Theeuwes, J. (2009). You do not find your own face faster; you just look at it longer. Cognition, 111(1), 114-122.
Gati, I., & Ben-Shakhar, G. (1990). Novelty and significance in orientation and habituation: A feature-matching approach. Journal of Experimental Psychology: General, 119(3), 251.
Gronau, N., Cohen, A., & Ben-Shakhar, G. (2003). Dissociations of personally significant and task-relevant distractors inside and outside the focus of attention: a combined behavioral and psychophysiological study. Journal of Experimental Psychology: General, 132(4), 512.
Hannula, D. E., Althoff, R. R., Warren, D. E., Riggs, L., Cohen, N. J., & Ryan, J. D. (2010). Worth a glance: using eye movements to investigate the cognitive neuroscience of memory. Frontiers in Human Neuroscience, 4.
Hannula, D. E., Baym, C. L., Warren, D. E., & Cohen, N. J. (2012). The eyes know eye movements as a veridical index of memory. Psychological Science, 23(3), 278-287.
Hannula, D. E., Ryan, J. D., Tranel, D., & Cohen, N. J. (2007). Rapid onset relational memory effects are evident in eye movement behavior, but not in hippocampal amnesia. Journal of Cognitive Neuroscience, 19(10), 1690-1705.
Heisz, J. J., & Shore, D. I. (2008). More efficient scanning for familiar faces. Journal of Vision, 8(1), 9-9.
Honts, C. R., Devitt, M. K., Winbush, M., & Kircher, J. C. (1996). Mental and physical countermeasures reduce the accuracy of the concealed knowledge test. Psychophysiology, 33(1), 84-92.
Jackson, M. C., & Raymond, J. E. (2008). Familiarity enhances visual working memory for faces. Journal of Experimental Psychology: Human Perception and Performance, 34(3), 556.
Lieblich, I., Kugelmass, S., & Ben-Shakhar, G. (1970). Efficiency of GSR detection of information as a function of stimulus set size. Psychophysiology, 6(5), 601-608.
Lykken, D. T. (1974). Psychology and the lie detector industry. American Psychologist, 29(10), 725.
Meijer, E. H., Selle, N. K., Elber, L., & Ben-Shakhar, G. (2014). Memory detection with the Concealed Information Test: A meta analysis of skin conductance, respiration, heart rate, and P300 data. Psychophysiology, 51(9), 879-904.
Millen, A. E., Hope, L., Hillstrom, A. P., & Vrij, A. (2017). Tracking the truth: the effect of face familiarity on eye fixations during deception. The Quarterly Journal of Experimental Psychology, 70(5), 930-943.
National Research Council (2003). The polygraph and lie detection. National Academies Press Washington, DC.
Norman, K. A., Polyn, S. M., Detre, G. J., & Haxby, J. V. (2006). Beyond mind-reading: multi-voxel pattern analysis of fMRI data. Trends in Cognitive Sciences, 10(9), 424-430.
Ohno, T., & Mukawa, N. (2004). A free-head, simple calibration, gaze tracking system that enables gaze-based interaction. In Proceedings of the 2004 symposium on Eye tracking research & applications (pp. 115-122). ACM.
Pedregosa, F., Varoquaux, G., Gramfort, A., Michel, V., Thirion, B., Grisel, O., . . . Dubourg, V. (2011). Scikit-learn: Machine learning in Python. Journal of Machine Learning Research, Oct. 12, 2825-2830.
Pertzov, Y., Manohar, S., & Husain, M. (2017). Rapid forgetting results from competition over time between items in visual working memory. Journal of Experimental Psychology: Learning, Memory, and Cognition, 43(4), 528.
Peterson, M. F., & Eckstein, M. P. (2013). Individual differences in eye movements during face identification reflect observer-specific optimal points of fixation. Psychological Science, 24(7), 1216-1225.
Peth, J., Kim, J. S., & Gamer, M. (2013). Fixations and eye-blinks allow for detecting concealed crime related memories. International Journal of Psychophysiology, 88(1), 96-103.
Pfeuffer, K., Vidal, M., Turner, J., Bulling, A., & Gellersen, H. (2013). Pursuit calibration: Making gaze calibration less tedious and more flexible. In Proceedings of the 26th annual ACM symposium on User interface software and technology (pp. 261-270). ACM.
Proudfoot, J. G., Jenkins, J. L., Burgoon, J. K., & Nunamaker Jr, J. F. (2016). More Than Meets the Eye: How Oculometric Behaviors Evolve Over the Course of Automated Deception Detection Interactions. Journal of Management Information Systems, 33(2), 332-360.
Rosenfeld, J. P., Labkovsky, E., Winograd, M., Lui, M. A., Vandenboom, C., & Chedid, E. (2008). The Complex Trial Protocol (CTP): A new, countermeasure-resistant, accurate, P300-based method for detection of concealed information. Psychophysiology, 45(6), 906-919.
Ryan, J. D., Hannula, D. E., & Cohen, N. J. (2007a). The obligatory effects of memory on eye movements. Memory, 15(5), 508-525.
Ryan, J. D., Hannula, D. E., & Cohen, N. J. (2007b). The obligatory effects of memory on eye movements. Memory, 15(5), 508-525.
Schwedes, C., & Wentura, D. (2012). The revealing glance: Eye gaze behavior to concealed information. Memory & Cognition, 40(4), 642-651.
Shalev-Shwartz, S., & Ben-David, S. (2014). Understanding machine learning: From theory to algorithms. Cambridge University Press.
Sokolov, E. N. (1963). Perception and the conditioned reflex.
Suchotzki, K., Verschuere, B., Van Bockstaele, B., Ben-Shakhar, G., & Crombez, G. (2017). Lying takes time: A meta-analysis on reaction time measures of deception.
Van Belle, G., Ramon, M., Lefévre, P., & Rossion, B. (2010). Fixation patterns during recognition of personally familiar and unfamiliar faces. Frontiers in Psychology, 1.
Verschuere, B., Meijer, E., & Ben-Shakhar, G. (2011). Memory detection: theory and application of the concealed information test. Cambridge University Press.
Vincent, E. (Mar. 25, 2016) Attacks of Nov. 13: November attacks: what Salah Abdeslam told investigators during his two-hour hearing. Le Monde, Retrieved and translated from http://www.lemonde.fr.
Yarbus, A. L. (1967). Eye movements during perception of complex objects. Springer.
Lancry-Dayan, O. C., et al. Do You Know Him? Gaze Dynamics Toward Familiar Faces on a Concealed Information Test. Journal of Applied Research in Memory and Cognition (2017).

\* cited by examiner

CONCEALED INFORMATION TESTING USING GAZE DYNAMICS

CROSS-REFERENCE TO RELATED APPLICATIONS

This application is a National Phase of PCT Patent Application No. PCT/IL2018/050514 having International filing date of May 10, 2018, which claims the benefit of priority of U.S. Provisional Patent Application No. 62/504,253, filed May 10, 2017, entitled "Accessing Concealed Memory Traces of Personally Familiar Objects Via Gaze Position Measurements", and of U.S. Provisional Patent Application No. 62/641,595, filed Mar. 12, 2018, entitled "Gaze Dynamics Towards Familiar Faces on a Concealed Information Test." The contents of the above application are incorporated herein by reference in their entirety.

BACKGROUND

The invention relates to the field of computerized concealed information tests.

The ability to detect concealed information, and specifically familiarity with specific people or objects, is highly important for both security and law enforcement purposes. A Concealed Information Test (CIT), versions thereof have existed for a few decades, assesses an examinee's crime-relevant memory on the basis of differences in physiological responses between crime-relevant and crime-irrelevant items. CIT is an alternative to polygraph testing, and is administered to prevent potential errors that may arise from the questioning style in a typical polygraph test.

In the CIT, an examiner presents several items to an examinee, one of which is a crime-relevant item. The items are selected such that innocent examinees would not be able to distinguish the crime-relevant (critical) item from the crime-irrelevant (non-critical) items. Each item is presented once in a block and this block is repeated several times in different presentation orders. During the CIT, the examiner records physiological responses to the items, such as skin conductance, heart rate, blood pressure, and respiration rate.

In the case that the responses do not differ between the critical and non-critical items, the examiner would infer that the examinee does not recognize the critical item. On the other hand, in the case that the responses differ between the critical and non-critical items, the examiner would infer that the examinee recognizes the critical item. Thus, the CIT can provide important forensic information for law enforcement agencies, identifying individuals with key information about a crime.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

Provided herein, in accordance with some embodiments, is a method that comprises operating a computerized controller to: administer an eye tracking-based concealed information test to a human subject; and administer to the human subject a short-term memory task at least partially in concurrence with the administering of the eye tracking-based concealed information test, to enhance accuracy of the eye tracking-based concealed information test.

Further provided herein, in accordance with some embodiments, is a method comprising operating a computerized controller to: operate a computer display to present images of objects, either simultaneously or one by one, at certain coordinates on said computer display; operate a camera to track eye movements of a human subject observing said computer display; compute at least one gaze parameter for each of the objects, based on the tracked eye movements and the certain coordinates, wherein the at least one gaze parameter is selected from the group consisting of: (a) a total dwell time on each of the objects, wherein the total dwell time is an accumulated time of all gaze fixations during an entire continuous period each of the objects has been presented, (b) a partial dwell time on each of the objects, wherein the partial dwell time is an accumulated time of all gaze fixations during a period that begins 0.5-2 seconds after each of the objects has started to be presented, (c) a number of visits to each of the objects, (d) a number of fixations on each of the objects, and (e) a mean duration of fixations on the objects; and determine that a certain one of the objects is familiar to the human subject if: (i) for gaze parameters (a)-(d), the at least one gaze parameter has a lower value for the certain one of the objects than for other ones of the objects, and (ii) for gaze parameter (e), the at least one gaze parameter has a higher value for the certain one of the objects than for other ones of the objects.

Further provided herein, in accordance with some embodiments, is a method for authenticating an identity of a human subject, comprising operating at least one hardware processor for: receiving a request from a user to be authenticated as a certain human subject; retrieving images of objects, wherein at least one of the objects is known to be familiar to the certain human subject, and at least one of the objects is known to be unfamiliar to the certain human subject; presenting to the user the images of the objects, either simultaneously or one by one; operating a camera to track eye movements of the user observing the presented images; computing at least one gaze parameter for each of the objects, based on the tracked eye movements and coordinates at which said images were presented, wherein the at least one gaze parameter is selected from the group consisting of: (i) a total dwell time on each of the objects, wherein the total dwell time is an accumulated time of all gaze fixations during an entire continuous period each of the objects has been presented, (ii) a partial dwell time on each of the objects, wherein the partial dwell time is an accumulated time of all gaze fixations during a period that begins 0.5-2 seconds after each of the objects has started to be presented, (iii) a number of visits to each of the objects, (iv) a number of fixations on each of the objects, and (v) a mean duration of fixations on the objects; determining which of the objects is familiar to the user and which of the objects is unfamiliar to the user based on: for gaze parameters (i)-(iv), the at least one gaze parameter having a lower value for the certain one of the objects than for other ones of the objects, and for gaze parameter (v), the at least one gaze parameter having a higher value for the certain one of the objects than for other ones of the objects; and authenticating the user as the human subject if the objects familiar and unfamiliar to the user are correspondingly known to be familiar and unfamiliar to the human subject.

Further provided herein, in accordance with some embodiments, is a method comprising: (a) operating a computer display to present, to a human subject, an image of an object; (b) operating said computer display to present a prompt that is designed such that the human subject is required to retrieve information on the object from its short-term memory in order to respond to the prompt; (c) receiving a response to the prompt from the human subject; (d) repeating steps (a) and (c), wherein, in every repetition, an image of a different object is presented in step (a); and (e) determining that one or more of the objects are familiar to the human subject based on at least one of: (i) the response by the human subject to the prompt is received faster for the one or more of the objects compared to other one or more of the objects, and (i) the response by the human subject to the prompt is more accurate for the one or more of the objects compared to other one or more of the objects. Optionally, the prompt includes, at random, the image of the object or an image of a different object, and requests the human subject to indicate whether the image of the object included in the prompt is the image of the object presented in step (a).

In some embodiments, the computerized controller: operates a computer display and a camera to administer the eye tracking-based concealed information test; and operates the computer display to administer the short-term memory task.

In some embodiments, the eye tracking-based concealed information test comprises: operating said display to simultaneously present images of objects at certain coordinates on said display; operating said camera to track eye movements of the human subject observing said display; computing at least one gaze parameter for each of the objects, based on the tracked eye movements and the certain coordinates, wherein the gaze parameter is selected from the group consisting of: (a) a total dwell time on each of the objects, wherein the total dwell time is an accumulated time of all gaze fixations during an entire continuous period each of the objects has been presented, and (b) a partial dwell time on each of the objects, wherein the partial dwell time is an accumulated time of all gaze fixations during a period that begins 0.5-2 seconds after each of the objects has started to be presented, (c) a number of visits to each of the objects, and (d) a number of fixations on each of the objects; and determining that a certain one of the objects is familiar to the human subject if the gaze parameter has a lower value for the certain one of the objects than for other ones of the objects.

In some embodiments, the short-term memory task comprises: after said display simultaneously presents images of the objects: presenting a prompt that relates to the images of the objects, and receiving a response to the prompt from the human subject.

In some embodiments, the prompt is designed such that the human subject is required to retrieve information from its short-term memory in order to respond to the prompt.

In some embodiments, the prompt includes presenting one of the images on said display, and the response includes an indication from the human subject as to whether said one of the images appeared in the simultaneous presentation of the images.

In some embodiments, the lower value is at least 20% lower.

In some embodiments, the higher value is at least 20% higher.

In some embodiments, the at least one gaze parameter is (a).

In some embodiments, the at least one gaze parameter is (b).

In some embodiments, the at least one gaze parameter is (c).

In some embodiments, the at least one gaze parameter is (d).

In some embodiments, the at least one gaze parameter is (e).

In some embodiments, the eye tracking-based concealed information test comprises: operating said display to present images of objects, one at a time, at certain coordinates on said display; operating said camera to track eye movements of the human subject observing said display; computing at least one gaze parameter for the objects, based on the tracked eye movements and the certain coordinates, wherein the gaze parameter is a mean duration of fixations on the objects; determining that a certain one of the objects is familiar to the human subject if the gaze parameter has a higher value for the certain one of the objects than for other ones of the objects.

In some embodiments, the short-term memory task comprises: after said display presents each of the images one at a time: presenting a prompt that relates to the respective image, and receiving a response to the prompt from the human subject. Optionally, the prompt is designed such that the human subject is required to retrieve information from its short-term memory in order to respond to the prompt.

Further provided herein, in accordance with some embodiments, is a system comprising: a camera; a display; a controller; and a non-transitory computer-readable storage medium having stored thereon instructions that, when executed by said controller, perform any one of the above methods.

Further provided herein, in accordance with some embodiments, is a computer program product comprising a non-transitory computer-readable storage medium having program code embodied therewith, the program code executable by at least one hardware processor to perform any one of the above methods.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION

Figure 1:
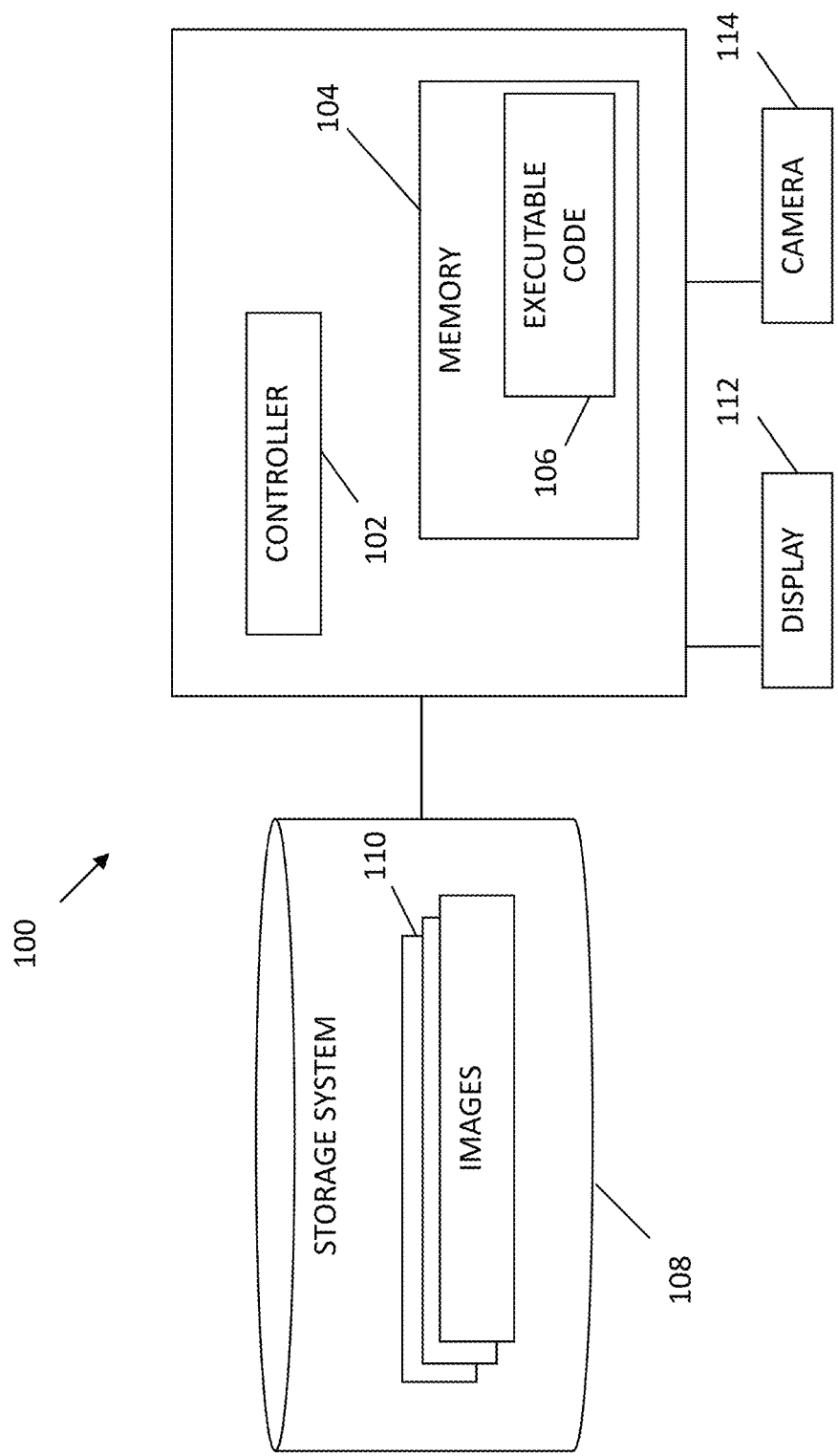
FIG. 1 is a block diagram of a computer system that may be used for concealed information testing, according to illustrative embodiments of the present invention.

Disclosed herein are a method, system, and computer program product for eye tracking-based concealed information testing, aimed at detecting certain information concealed by a human subject.

The terms "concealed information", "concealed memory", "concealed familiarity", and "concealed knowledge", as may be used herein interchangeably, refer to a specific piece of information preexisting in a human subject's memory, which the subject intentionally attempts to conceal from others, such as in the case of a suspected criminal or terrorist attempting to conceal certain information from law enforcement.

Embodiments of the present invention are directed to a visual concealed information test, utilizing an eye tracker that constantly tracks the point of gaze of the subject while the subject is being presented with certain visual stimuli. The visual stimuli may include images of both items unfamiliar to the tested subject, and items suspected to be familiar to the subject but concealed by him or her. The images may depict, for example, human faces, geographical sites, physical objects, and/or the like.

The terms "point of gaze" or "gaze position", as used herein interchangeably, refer to a location that a subject is looking at, such as a location on a computer screen or on a surface over which certain visual information is presented. The term "fixation", as used herein, refers to a stable gaze position over a certain duration of time, termed "fixation period" or "fixation duration". The term "saccade", as used herein, refers to a fast and brief shift of gaze position, as known in the art; saccades typically occur between fixations. The term "dwell time", as used herein, refers to the accumulated time of all fixations on a certain point of gaze or on a group of adjacent points of gaze, such as points that are all within the coordinates of a single object presented to the subject. The term "visits", as used herein, refers to a number of times a particular object was gazed on; a single "visit" contains all consecutive fixations on the particular object before the subject's gaze travels outside of the coordinates of that object. The above defined terms are referred to herein generally as "gaze parameters".

Detection of the concealed information is made, inter alia, based on automatic, computerized detection of one or more of the following surprising phenomena discovered by the inventors:

First, when a subject is simultaneously presented with images of multiple objects, the dwell time on a familiar object will be substantially shorter than on a non-familiar object.

Second, in the above scenario, detection of the concealed information may be even further enhanced by dividing the dwell time measurements into two phases: a first phase, lasting approximately 0.5-2 seconds, or more specifically 0.7-1.3 seconds, from the moment the images are first presented; and a second phase which begins immediately after the first phase and lasting until the images cease to be presented (or earlier, e.g., for 2-15 additional seconds after the first phase). In the first phase, dwell time is longer on familiar objects than unfamiliar objects, but might be approximately equal when the subject employs countermeasures (i.e., makes an effort to gaze equally on all objects). In the second phase, whether countermeasures are employed or not, the subject will dwell longer on unfamiliar objects than on familiar objects, essentially "avoiding" the familiar ones. Namely, observing the subject's gaze in the second phase may be reliably indicative on whether the object in question is familiar or not.

Third, in the above scenario, fewer visits are made to familiar objects than to unfamiliar objects.

Fourth, in the above scenario, the number of fixations (also "fixation count") on an object during the entire time the multiple objects are displayed is smaller for familiar objects compared to unfamiliar ones.

Fifth, when a subject is presented with only a single object at a time, the mean duration of fixations on the object (namely, fixations on coordinates within the displayed object) is longer for familiar objects compared to unfamiliar ones.

Sixth, in an eye tracking-based concealed information test (such as the one disclosed herein, or a differently-arranged test), the ability of the subject to circumvent the results by consciously controlling their eye movement (i.e., employing "countermeasures") is greatly diminished by integrating the test with a short-term memory task. This holds true both for tests in which multiple objects are presented simultaneously, and for tests in which only a single object is presented at a time. When only a single object is presented, however, there is an added benefit to the integration with a short-term memory task: the task is completed more accurately and/or more quickly when the object included in a prompt of the task is familiar compared to when the object is unfamiliar.

In some embodiments, only a single one of these phenomena is used to reliably conclude what is the concealed information.

In some embodiments, only the occurrence of two or more of these phenomena is used to reliably conclude what is the concealed information. Optionally, the occurrence of one or more of the first to fifth phenomena, in the course of a concealed information test integrated with a short-term memory task (the sixth phenomena), is used to reliably conclude what is the concealed information.

In some embodiments, only the occurrence of all phenomena is used to reliably conclude what is the concealed information.

Reference is made to FIG. 1, showing a block diagram of an exemplary computing system 100 that may be used for concealed information testing, according to some embodiments of the present invention. As shown, computing system 100 may include a controller 102, such as a hardware processor or a plurality of hardware processors. Computing system 100 may further include a non-transient memory 104 storing executable code 106, as well as a storage system 108 that may store images 110. Storage system 108 may be physically co-located with other components of computing system 100, or may be accessible to it via a network connection. Computing system 100 may further include a computer display 112 or a different means for visual display, such as a projector. Computing system 100 may further include an eye tracker such as a camera 114 capable of imaging eye movement, or a different optical device capable of imaging eye movement.

Executable code 106 may include any type of computer-readable instructions that, when executed by one or more hardware processors of controller 102, cause computing system 100 to perform the various functions described herein. For example, executable code 106 may be a software application for detecting concealed information.

Although not shown, any input/output (I/O) components may be included, or connected to, computing device 100.

For example, I/O components may include a pointing device (e.g., a mouse), a keyboard, one or more speakers, a wired or wireless network interface card (NIC), and/or the like.

Some embodiments of the invention detect concealed information by analyzing certain gaze patterns that have been determined by the inventors to be a reliable indicator of a subject's cognitive reaction to familiar and unfamiliar objects shown to him or her.

For example, some embodiments present to the subject, on display 112, a series of images 110 that depict certain objects, such as human faces. Eye movements of the subject are recorded by an eye tracker (referred to herein as camera 114, for simplicity of discussion) that is directed towards the subject's eyes.

Controller 102 may retrieve some of images 110 from storage system 108, and displays them on display 112 at certain coordinates. For simplicity of discussion, those displayed images are interchangeably referred to as "objects", for the objects they depict.

Camera 114, operating in concert with controller 102, then tracks the subject's eye movement relative to the coordinates of the images displayed on display 112. Controller 102 can then determine one or more gaze parameters such as gaze position, fixation, fixation duration, saccades, and/or dwell time, with respect to each of the objects displayed.

Controller 102 may then compare these determined gaze parameters with predetermined thresholds, ratios, and/or other measures, to output an indication of which of the displayed objects, if at all, are familiar to the subject.

Computer system 100 may be implemented, for example, in:

1. A kiosk positioned at locations where security screening of persons is needed, such as airports, train stations, government buildings, etc.

2. A stationary or portable computing device positioned in interrogation rooms of either law enforcement or civilian institutions.

3. A portable computing device, such as a smart phone, a tablet computer, a smart watch, a wearable computer, or a notebook computer which belongs to the subject, and used for purposes of authenticating the subject's identity before accessing certain computer resources (e.g., the device itself, an Internet website, a restricted-access facility, etc.).

Figure 2:
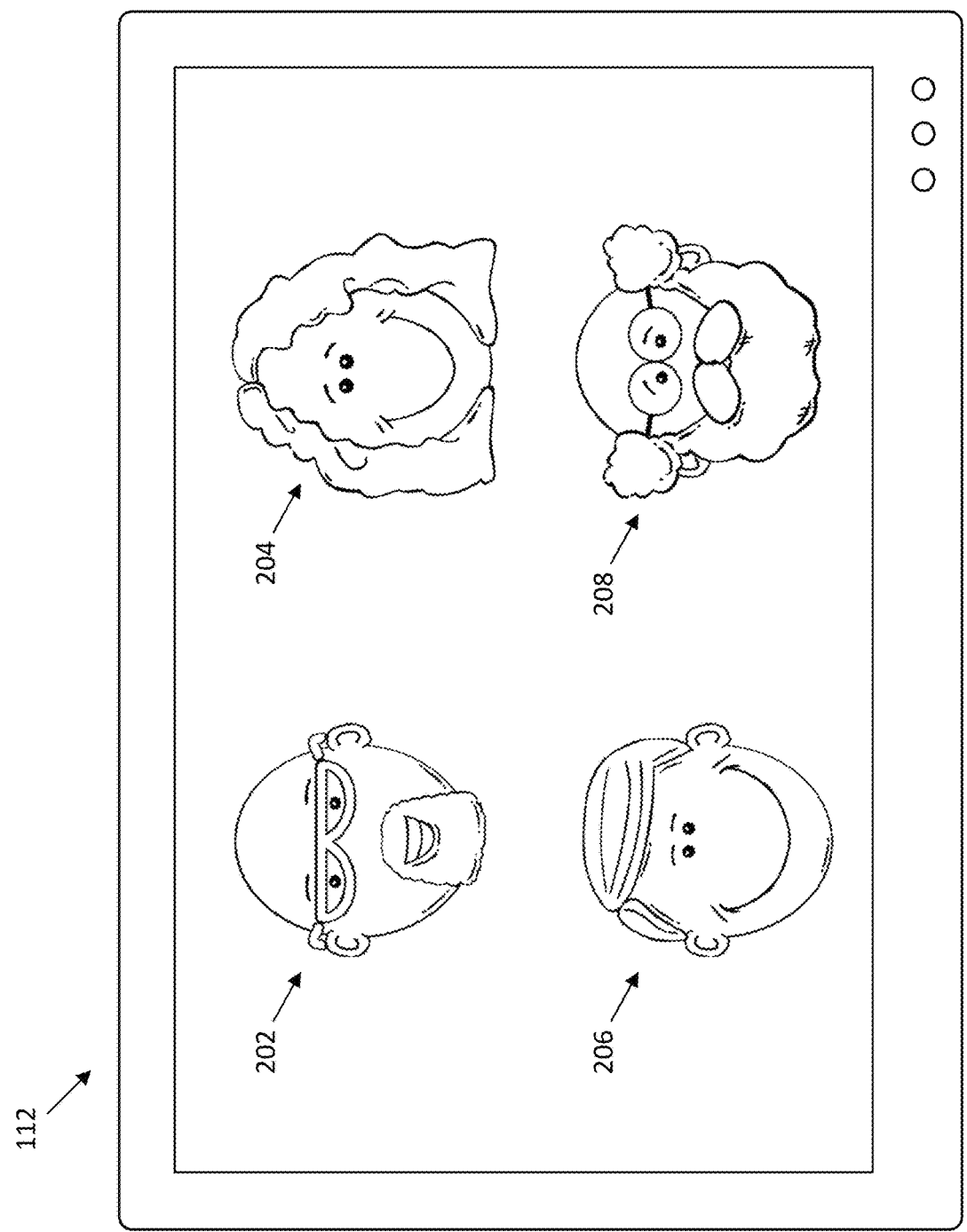
FIG. 2 schematically illustrates how multiple images may be displayed on a display of the system of FIG. 1, according to illustrative embodiments of the present invention.

Reference is made to FIG. 2, which schematically illustrates how multiple images may be displayed on display 112. Four faces 202, 204, 206, and 208 are shown, and are arranged in a 2×2 matrix.

Similarly, a larger number of objects (such, but not limited to, faces), such as 5, 6, 7, 8, 9, 10, 11, 12, 13, 14, 15, 16, or more, may be arranged in a matrix of X over Y, wherein at least one of X and Y is 1 or larger, and the other one of X and Y is 2 or larger; these arrangements are not shown.

Alternatively, the objects may be arranged not in a matrix but rather randomly, or over a predetermined path (such as a circular path, an ellipsoidal path, a spiral path, etc.); these arrangements are not shown.

Each object may be displayed at a size large enough to enable its recognition by the subject, depending on the distance of the subject from display 112, the visual acuity of the specific subject, etc.

As briefly discussed above, the images may depict, for example, human faces, geographical sites, physical objects, and/or the like. In case mass screening of a large number of people is required, such as in airports, train stations, government buildings, or the like, the displayed images may include objects which a typical terrorist, criminal, or other individual with malicious intent might want to conceal. For example, such images may depict certain weapons, explosives, or other items which the general population is unlikely to be familiar with, but a malicious subject is not. In individual interrogation scenarios, when the interrogating authority has some background knowledge on the test subject, a subject-specific concealed information test may be devised. This test may include, for example, images of faces of known terrorists, which the interrogators suspect the subject is related to. As another example, such test may include images of geographical sites which the subject is suspected to have visited before but is denying the fact.

Figure 3:
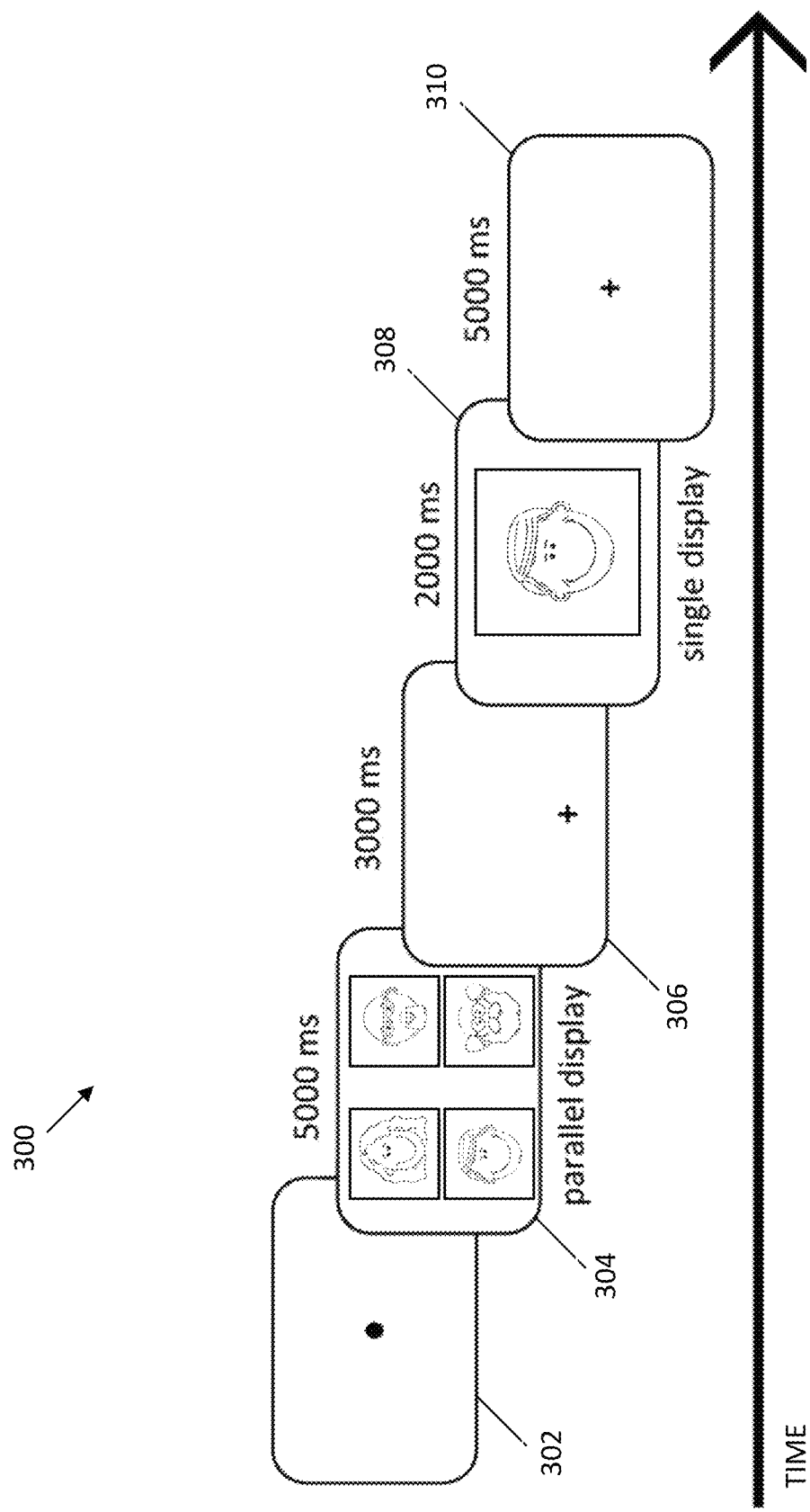
FIG. 3 shows an exemplary Graphical User Interface (GUI) sequence which integrates an eye tracking-based concealed information test with a short-term memory task, according to some embodiments of the invention.

Reference is now made to FIG. 3, which shows an exemplary GUI sequence 300 which integrates an eye tracking-based concealed information test (such as the test of the present disclosure, or a different test) with a short-term memory task, in order to enhance the accuracy of the test. The first, second, third, and fourth phenomena are applicable to this exemplary GUI sequence.

The short-term memory task discussed herein is merely an exemplary one, and a different short-term memory task may be advantageously integrated with the eye tracking-based concealed information test in order to enhance its accuracy. The term "short-term memory task" is to be construed as any task which: (a) presents the test subject with a prompt relating to one or more images that were shown to the subject immediately prior to the question (e.g., 0-15 seconds prior), wherein this prompt is designed to require the subject to retrieve information as to the one or more images from his or her short-term memory, and (b) receives a response to the prompt from the subject. The prompt may be textual and/or vocal, and include instructions to the subject to respond to a question (open-ended or close-ended) or perform a task (e.g., use an input device, such as a keyboard, mouse, and/or microphone, to interact with the computer system) related to the previously-shown images.

For example, the short-term memory task may be a delayed-estimation task, as known in the art. See, e.g., the task shown in FIG. 1 of Ma W J, Husain, Bays, "Changing concepts of working memory", Nat Neurosci. 2014 March; 17(3):347-56. As another example, the short-term memory task may be a continuous response task, as known in the art. See, e.g., Zhou, Mondloch, Emrich, "Encoding differences affect the number and precision of own-race versus other-race faces stored in visual working memory", Attention, Perception, & Psychophysics (2018) 80:702-712.

The instructions included in the prompt optionally conceal the fact that this is a concealed information test, and only instruct the test subject on how to perform the short-term memory task.

GUI sequence 300 optionally begins with an empty display 302, or a display of introductory information to the test subject, such as the aforesaid instructions. The sequence proceeds to the next step once the subject is in view of the camera, and eye tracking can technically start.

Then, a simultaneous (also "parallel") display 304 of multiple objects is presented to the subject for a certain duration, such as between 300-15,000 milliseconds, or any value therebetween, or any larger value. This may be the object arrangement discussed in connection with FIG. 1, for example. While the multiple objects are displayed, the camera tracks the subject's eye movements, and the controller can thereafter compute the one or more gaze parameters.

Then, optionally, a blank display 306 (or a display which at least does not show any of the objects previously displayed) is shown for a certain duration, such as between 300-15,000 milliseconds, or any value therebetween, or any larger value.

Next, a display 308 with one of the objects previously presented, or with a different object, is shown for a certain duration, such as between 300-15,000 milliseconds, or any value therebetween, or any larger value. The test subject is requested to indicate, during an additional allotted timeframe 310 of, for example, 300-15,000 milliseconds or any value therebetween, or any larger value, whether the presented object was presented previously. This is the short-term memory task, which ensures that the test subject stays focused on activating his or her short-term memory while the concealed information test is being administered.

GUI sequence 300 may be repeated multiple times with different images, to provide additional eye tracking data for analysis and computation of the gaze parameters.

In case a malicious test subject, such as a criminal or a terrorist, attempts to circumvent the results of this concealed information test, he or she will be faced with the following problems: If the subject ignores the short-term memory task in an attempt to free up cognitive resources to avoid suspicious gaze patterns on familiar and unfamiliar objects, the subject will score poorly on the short-term memory task. This, on its own, may signal to the testing authority, (e.g., law enforcement) that the test subject has a malicious intent to conceal certain information. The same applies to a subject who completely refuses to take the concealed information test. Such behaviors by the subject would entail similar repercussions to a suspect refusing to cooperate in an interrogation or refusing to take a polygraph test. In some scenarios, such as when mass screenings of people need to be performed (e.g., at an airport), this may be a sufficient indication that this particular subject had failed the screening and needs to be processed through additional interrogation to strengthen or refute the concern. Even if the subject managed to both succeed on the short-term memory task and somewhat control his or her gaze patterns on familiar and unfamiliar objects, experiments conducted the inventors (discussed below) confirm that the gaze parameters of the present invention, singularly or in any combination, may be sensitive enough to detect object familiarity even given cognitive countermeasures employed by a malicious subject.

As an alternative to GUI sequence 300 of FIG. 3, which is based on presenting multiple objects simultaneously, a different GUI sequence (not shown) may be used. In this alternative sequence, only one object at a time is displayed (which could be a familiar or unfamiliar object), followed by a prompt that is part of a short-term memory task. This repeats itself a number of times, so that, in total, the subject had looked at images of at least one object suspected to be familiar to the subject, and of some objects likely unfamiliar to the subject. The fifth phenomenon described above is applicable to this alternative GUI sequence.

Reference is now made back to FIG. 1. Computerized system 100 may operate according to the following method, implemented in executable code 106:

Display 112 may be operated to simultaneously present images of objects at certain coordinates on the display, or to present an image of a single object at a time.

Camera 114 may be operated to track eye movements of a human subject who observes display 112.

Controller 102 may compute one or more gaze parameters for each of the objects, based on the tracked eye movements and the certain coordinates. Optionally, controller 102 associates the coordinates of display 112 with eye movements acquired by camera 114 during a preliminary calibration phase, as known in the art.

Controller 102 may then determine (or at least estimate) that a certain one of the objects is familiar to the human subject if one or more of the following holds true:

1. In accordance with the first phenomenon, a total dwell time on the certain one of the objects is shorter than a total dwell time on other ones of the objects. "Total" refers to dwell time during the entire continuous period the object was displayed. The term "shorter", in this context, means at least 20%, 30%, 40%, or 50% shorter, or any percentage value therebetween.

2. In accordance with the second phenomenon, dwell time specifically in the second phase is shorter on the certain one of the objects than on other ones of the objects. The term "shorter", in this context, means at least 20%, 30%, 40%, or 50% shorter, or any percentage value therebetween.

3. In accordance with the third phenomenon, the number of visits to the certain one of the objects is smaller than to the other ones of the objects. The term "smaller", in this context, means at least 20%, 30%, 40%, or 50% smaller, or any percentage value therebetween.

4. In accordance with the fourth phenomenon, the number of fixations on the certain one of the objects, during the entire time the multiple objects were displayed, is smaller than on the other ones of the objects. The term "smaller", in this context, means at least 20%, 30%, 40%, or 50% smaller, or any percentage value therebetween.

5. In accordance with the fifth phenomenon, which applies when the subject is presented with only a single object at a time, the mean duration of fixations on the certain one of the objects is longer compared to other ones of the objects. The term "longer", in this context, means at least 20%, 30%, 40%, or 50% longer, or any percentage value therebetween. Alternatively, instead of the mean, a median is used.

6. In accordance with the sixth phenomenon, which applies when the subject is presented with only a single object at a time, the subject's response to the prompt of the short-term memory task is more accurate and/or quicker when that object is also included in the prompt, compared to when a different object is included in the prompt. The terms "more accurate" and "quicker", in this context, means at least 20%, 30%, 40%, or 50% more accurate and/or quicker, or any percentage value therebetween. For example, the prompt may include an image of the object presented immediately before, or an image of a different object—at random. The prompt instructs the subject to answer whether the image included in the prompt is of the object previously displayed or not. This requires the user to retrieve information from short-term memory. When repeating the presentation, prompt, and response stages multiple times (e.g., 2-20 times), such that the random image included in the prompt is sometimes of an object assumed to be unfamiliar to the subject and sometimes of an object suspected to be familiar to the subject, familiar objects are likely to be those whose associated prompt was answered more quickly and/or more accurately by the subject.

Following a determination or estimation that a certain one of the objects is familiar to the human subject, controller 102 may issue an indication of that certain object, such as a visual or an audible indication. The indication is optionally made only to a supervisor of the test, and not to the test subject. Alternatively, the indication is made only to the test subject. Further alternatively, the indication is made both to the test subject and to the supervisor of the test.

In addition to or instead of the indication, controller 102 may carry out an action such as granting the subject access to a certain physical location or a computerized resource if a determination or estimation was made that none of the objects is familiar to the human subject, or that object(s) found familiar to the human subject do not indicate any malicious intent. The granting of access may include, for example, unlocking and/or opening a door or a gate using an electrical signal transmitter by controller 102 to the door/gate or to a device controlling the door/gate. It may include logging the subject into a restricted computerized resource, such as a server computer in a network, a personal computer, a portable computing device, and/or the like. Accordingly, provided herein is also a method for authenticating an identity of a human subject, which includes the following steps:

First, receiving a request from a user to be authenticated as a certain human subject. For example, a user may enter a certain username (and optionally also a password) into a computerized system he or she wishes to access, where this username belongs to a certain human subject. However, the system is still unsure whether the user who entered the username is indeed its real owner. Accordingly, the following steps of the method may improve the reliability of the authentication, much like two-factor authentication, for example, is used to enhance user authentication.

Then, images of objects may be retrieved from a computer memory, wherein at least one of the objects is known to be familiar to the certain human subject and at least one of the objects is known to be unfamiliar to the certain human subject. For example, the human subject may have previously provided, e.g., during an enrollment stage, images of objects he or she are familiar with.

The objects may then be displayed to the user in parallel or one at a time, as discussed above.

A camera is operated to track eye movements of the user as he or she observe the presented images.

At least one hardware processor is then operated to compute one or more gaze parameters for each of the objects, based on the tracked eye movements and coordinates at which said images were presented.

The at least one hardware processor is then operated to determine which of the objects is familiar to the user and which of the objects is unfamiliar to the user, based on the gaze parameter having a lower or higher value for a familiar object compared to an unfamiliar object, as discussed above.

Finally, the user is authenticated as the human subject if the objects familiar and unfamiliar to the user are correspondingly known to be familiar and unfamiliar to the human subject.

For scenarios where authentication is needed before granting the user access to a particular computing device, all of the steps of this authentication method may be carried out the device itself. For scenarios where authentication is needed before granting the user access, through a local computing device, to a remote server computer, the steps may be divided between the local computing device and the remote server computer: The remote server computer may carry out the receiving of the request from the user to be authenticated, and the final authentication of the user as the human subject; the local computing device may carry out the rest of the steps—the operating of the camera, the computation of the gaze parameter(s), and the determining of which of the objects is familiar and which of the objects is unfamiliar to the user. Alternatively, given various security policies, the division of steps between the local computing device and the remote server computer, may be different than that. Further alternatively, one or more additional computing device may participate in executing the method.

For simplicity of discussion, this method for authentication has been described without repeating those descriptions already provided earlier in this disclosure, such as with respect to the camera, hardware processor, image types, gaze parameters, etc. These descriptions apply here.

Optionally, controller 102 administers to the human subject a short-term memory task at least partially in concurrence with presenting the images and tracking the eye movements, in order to enhance accuracy of the determination that the certain one of the objects is familiar to the human subject. Exemplary short-term memory tasks that are suitable for this embodiment have been discussed above.

In a different embodiment, computerized system 100 may be used to execute a different eye tracking-based concealed information test, and to administer to the test subject a short-term memory task at least partially in concurrence with the administering of the different eye tracking-based concealed information test, in order to enhance accuracy of the eye tracking-based concealed information test.

In some embodiments, the detection of the concealed information (e.g., which object is familiar to the subject) is not based on any of the following parameters, which are often used in traditional concealed information tests and polygraphy tests: skin conductance, heart rate, blood pressure, and respiration rate. In other embodiments, the detection of the concealed information may be partly based on one or more of these parameters, in order to enhance accuracy.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. Rather, the computer readable storage medium is a non-transient (i.e., not-volatile) medium.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The description of a numerical range should be considered to have specifically disclosed all the possible subranges as well as individual numerical values within that range. For example, description of a range from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The descriptions of the various embodiments of the present invention are being presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Experimental Results

Experiments conducted and described herein demonstrate the usability and efficacy of embodiments of the invention. Some embodiments of the invention may be configured based on certain experimental methods and/or experimental results; therefore, the following experimental methods and/or experimental results are to be regarded as embodiments of the present invention. The experiments described herein clearly demonstrate that methods according to some embodiments of the invention provide efficient detection of concealed information, optionally even when countermeasures are applied, namely—when test subjects are explicitly told how to control their eye movements when they see familiar and unfamiliar objects.

Some of the experiments revealed that, when attempting to memorize a number of pictures of faces in the framework of a unique short-term memory task, participants' gaze was initially directed towards a personally familiar face, followed by a strong avoidance of it. This avoidance was evident even when participants were instructed to conceal their familiarity and direct their gaze equally at all faces. Participants were only partially able to control the initial preference to fixate on the familiar face.

In three experiments conducted, four faces were presented on a screen (e.g., as shown by FIGS. 2 and 3) followed by the presentation of a single face. Participants were required to report whether the single face had appeared in the previous display. Some of the faces were pictures of familiar people, taken from the participants' Facebook® accounts. One of the findings was that when several faces are displayed, people tended to look less at the familiar face, even when they were asked (or where otherwise motivated) to conceal recognition of the faces that were familiar to them. Moreover, this pattern was observed even when subjects were instructed to look equally at all faces. Exploiting these findings, embodiments of the invention exhibit impressive detection efficiency, suggesting practical applications when there is a need to detect concealed familiarity, e.g., in security and forensic settings.

An improvement to the field of eye tracking-based concealed information testing, and not limited to the specific eye tracking-based concealed information test discussed herein, were made by incorporating a unique short-term memory task into the test. According to this short-term memory task, after seeing a display of four faces, participants see a single face and are asked to decide whether this face appeared in the previous display. This task exploits the advantages of eye tracking and enables the use of simultaneous presentation of stimuli, unlike many classic concealed information test procedure which relies on a serial presentation of single items. This unique short-term memory task has two major advantages:

First, in contrast to most previous research which used familiarity judgment tasks, this unique short-term memory task is orthogonal to the familiarity of the faces (i.e., the completion of the task does not depend on the degree of familiarity); hence, participants are not required to make different manual responses (i.e., key presses) to personally familiar and unfamiliar faces. However, based on previous findings on the interaction between short-term and long-term memory, this paradigm has proven to maximize differences in viewing behavior during encoding of familiar and unfamiliar faces. Since familiar objects are expected to require fewer resources during encoding into short-term memory, they should attract less attention than unfamiliar items. This difference should manifest itself in eye movements, and result in more fixations at unfamiliar faces.

Second, the focus of participants on the short-term memory task potentially makes it harder for them to volitionally control their eye movements and conceal their familiarity.

In addition to the unique short-term memory task, a new analysis tool for eye tracking-based concealed information testing was used; besides the standard method used in concealed information testing research to evaluate detection efficiency (signal detection measures), a classification algorithm (support vector machine (SVM)) was used. This algorithm was drawn from the machine learning domain and was used to classify stimuli as familiar vs. unfamiliar using multiple eye tracking measures. This method has been shown to be highly useful in neuroimaging research and yielded high classification accuracy rates when applied to concealed information testing.

The only difference between the three experiments was the concealment instructions. Participants in the first experiment were only instructed to perform the short term memory task (referenced as "non-concealed"—NC). In the second experiment, participants were also instructed to "conceal their familiarity with the faces", without explicitly explaining how to conceal (referenced as "concealed"—C). Finally, the third experiment included concise instructions regarding how to conceal familiarity—"In order to conceal your familiarity with the pictures, avoid looking at the familiar face first and try to look at all the faces equally" (referenced as "countermeasures"—CM).

Each of the three experiments included 29 participants (NC: 12 males, C: 8 males, CM: 6 males, ranging in age from 21 to 28) all of whom had normal or corrected to normal vision. In the non-concealed experiment, 40 people registered for the experiment, of whom 5 were no-shows, 4 had calibration problems, 1 was not presented with familiar faces due to a human error and 1 had too many disqualified pictures; namely, unfamiliar faces that were classified as familiar in the debriefing, or vice versa (3.5 SD above the average), resulting in a total of 29 participants. In the concealed experiment, 36 people registered for the experiment, of whom 4 were no-shows and 3 had calibration problems, resulting in total of 29 participants. In the countermeasures experiment, 32 people registered for the experiment, of whom 2 were no-shows and 1 asked to stop the experiment due to discomfort, resulting in total of 29 participants. The sample size in all three experiments relied on a power analysis, which indicated that a sample of 27 participants would be sufficient to detect a one-tailed medium effect size (d=0.5) with a power of 0.8. The one-tailed hypotheses were derived from a pilot study conducted prior to the experiments mentioned herein.

In order to use realistic stimuli (the parallel display of four images), photos of acquaintances of the participants taken from their Facebook® account were used. Prior to the experiment, participants filled in a questionnaire in which they supplied the names of eight women and eight men they know and, rated their familiarity with each person on a scale from 1 (meet approximately twice a year or less) to 5 (meet on a daily basis). For each participant, four pictures of women and four of men were taken with permission from public pictures on Facebook®. Pictures with a straightforward head position were selected, transformed into black and white images, and normalized to have similar average brightness using Matlab (MATLAB 8.6, The MathWorks Inc., Natick, Mass., 2015).

The pictures of eight participants were grouped together to generate the stimulus sets for the parallel display, resulting in a total of 64 pictures in each set, with 8 familiar faces and 56 unfamiliar faces for each participant (the unfamiliar faces consisted of the 8 familiar faces of the other 7 other participants in the same cohort). This design ensured that the faces were counterbalanced, such that the familiar faces of each participant were the other participants' unfamiliar faces. For the single display, the pictures of four participants were grouped together, resulting in a total of 32 pictures in each set, repeated twice during the experiment (in total, 64 trials). The 32 pictures consisted of 8 familiar faces and 24 unfamiliar faces for each participant (the unfamiliar faces consisted of the 8 familiar faces of the other 3 participants in the same cohort). Accordingly, the eight participants in each group saw the same parallel displays with half of them also seeing the same single displays.

The stimuli were displayed on a 23" Syncmaster monitor, with a 104 Hz refresh rate, and a 1024×768 screen resolution. Monocular gaze position was tracked at 1000 Hz with an Eyelink 1000+(SR Research Ltd., Mississauga, Ontario, Canada). Participants' heads were stabilized using a chinrest, situated 60 cm from the screen.

The short-term memory task consisted of 64 trials. At the beginning of the experiment, each participant went through the standard nine-point calibration and validation procedure provided with the eye tracker. Each participant completed at least 3 correct practice trials out of five. Participants that failed more than 2 out of the 5 trials underwent another session of five training trials (no participant needed more than two practice sessions). The practice session was designed to train the participants to adequately perform the short-term memory task and used a different set of unfamiliar faces taken from Facebook. Thus, none of the stimuli in the practice sessions was used later in the real experiment. In the experiment, all trials started with a fixation validation process, allowing a deviation of only 1 degree of visual angle between the predicted gaze position and the center of fixation point. Larger deviations were accompanied by an error beep and led to a repeated calibration process. Fixation validation was followed by a parallel display of four faces (5000 ms), followed by a blank fixation interval (3000 ms), a single face display (2000 ms) and a blank screen with a central fixation point (5000 ms), e.g., as shown by FIG. 3 and described herein. The fixation point prior to the single display was displayed below the face in order not to bias gaze position to any specific location on the face. During the single face display, participants were required to press one of two keys according to whether the current face had been presented in the previous parallel display. The correct answers in half of the trials were "yes" and in the other half "no", in random order. No response was requested from the participants during the parallel display.

A familiar face could be displayed on the parallel display, the single display, both displays, and none of these. In the parallel display, half of the trials consisted of only unfamiliar faces and the other half consisted of one familiar and three unfamiliar faces. Accordingly, each familiar face appeared in four trials, once in each location of the parallel display (top right, top left, bottom right, bottom left). The familiar face was pseudo-randomly assigned to three unfamiliar faces, resulting in a different combination of faces in every trial. In the single display, each familiar face appeared twice, once when the answer to the short-term memory task was "yes" and once when it was "no". Because the familiar faces of one participant were the unfamiliar faces of another participant, all faces appeared once in each location in the parallel display and twice in the single display. This design ensured that all faces were completely counterbalanced, such that each face appeared equally in all possible locations and displays. Overall, there were 16 trials in each of the four following combinations: 1) familiar present in the parallel display, familiar present in the single display 2) familiar present in the parallel display, familiar absent in the single display 3) familiar absent in the parallel display, familiar present in the single display and 4) familiar absent in the parallel display and familiar absent in the single display.

During the debriefing, all participants were required to report whether the 64 pictures in their dataset were familiar or not. Pictures were discarded from further analysis if participants marked them as familiar on the pre-experiment questionnaire but did not recognize their picture during the debriefing, or if they were recognized during the debriefing but were not included in the list of familiar faces supplied in the pre-experiment questionnaire (overall 2.8%, 1.3% and 2.1% of the pictures in the non-concealed, concealed and countermeasures experiments, respectively).

Figure 4:
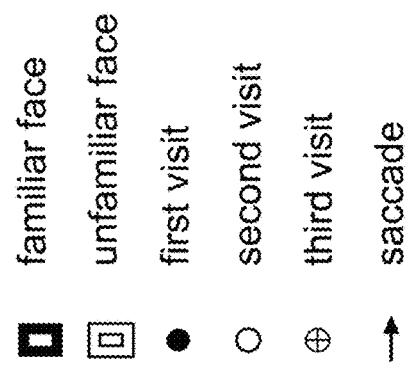
FIG. 4 illustrates eye movement data of two test subjects, in accordance with experimental results.
Figure 4:
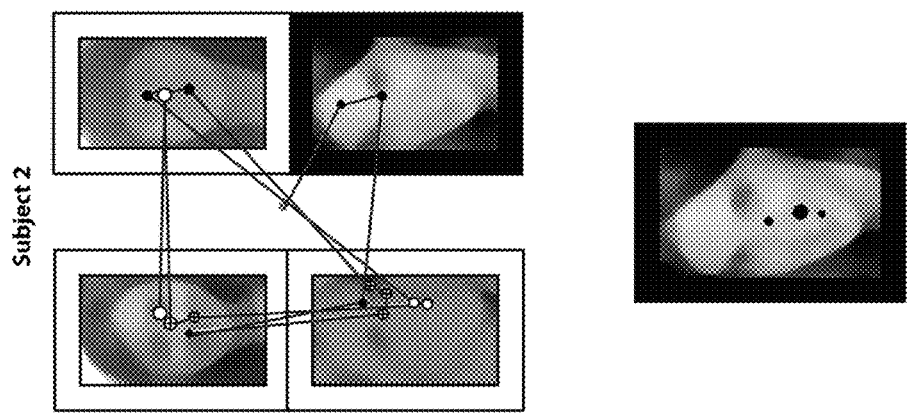
Figure 4:
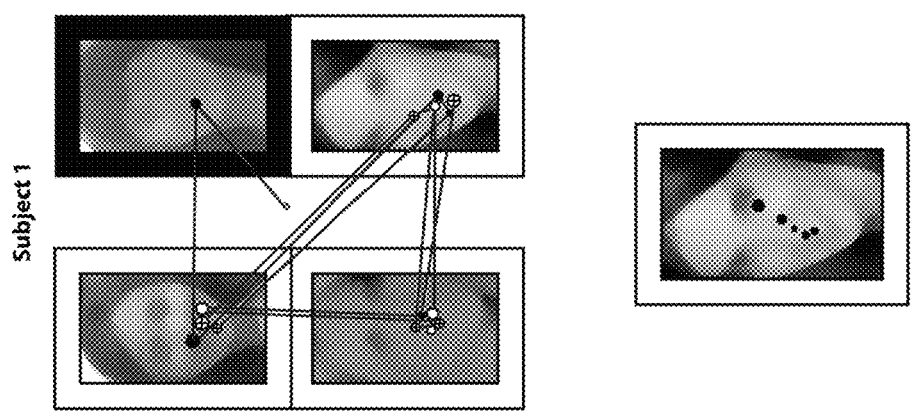

Eye movement data were parsed into saccades (see, for example, FIG. 4, which shows saccades of two test subjects) and fixations using EyeLink's standard parser configuration: samples were defined as a saccade when the deviation of consecutive samples exceeded 30°/second velocity or 8,000°/second$^2$ acceleration. Samples gathered from time intervals between saccades were defined as fixations.

The following measures were extracted in each trial during the parallel display: gaze dwell time during the first phase (1-1000 ms), the second phase (1000-5000 ms), number of visits, and the total number of fixations on each picture. The two phases are based on a pilot study which showed a preference for the familiar item during the initial second of the display, followed by an avoidance phase afterwards. The measures that were extracted during the single display were the mean fixation duration, response time (RT) and accuracy on the short-term memory task.

In order to create a single detection measure for each participant, the four measures based on the results from the parallel display were used, namely: dwell time on the first and second phases, number of visits and total fixation count, and the results from the single display: mean fixation duration and reaction time in the memory task. These are shown in Table 1 below.

TABLE 1

Definition of the different ocular measures used in the statistical analysis

| | Measure | Description |
|---|---|---|
| Parallel display | Dwell time, first phase | Total time (in ms) that gaze was directed to an area during the first interval of the trial (0-1000 ms). |
| | Dwell time, second phase | Total time (in ms) that gaze was directed to an area during the second interval of the trial (1000-5000 ms (end of trial)). |
| | Number of visits | Number of times each face area was visited. A single visit consists of all consecutive fixations on a specific area before moving out of that area. |
| | Fixation count | Number of fixations on a face during the whole display time. |
| Single display | Mean duration of fixation | Mean duration of all the single fixations. |

To assess the gaze position dynamics throughout the trial, a time course analysis was conducted. Only trials consisting of familiar faces were included. Each trial was parceled into 100 ms bins and in each time bin the proportion of time that gaze was directed to each of: familiar faces, unfamiliar faces and outside of any interest area/blinks were calculated. Dwell time on the three unfamiliar faces was pooled and divided by three to make it comparable to the dwell time on the familiar face. For each time bin, the dwell time on the familiar faces was contrasted with the dwell time on unfamiliar faces and a correction for multiple comparisons was applied using the False Discovery Rate (FDR). The time courses of all the participants were averaged.

Figure 5A:
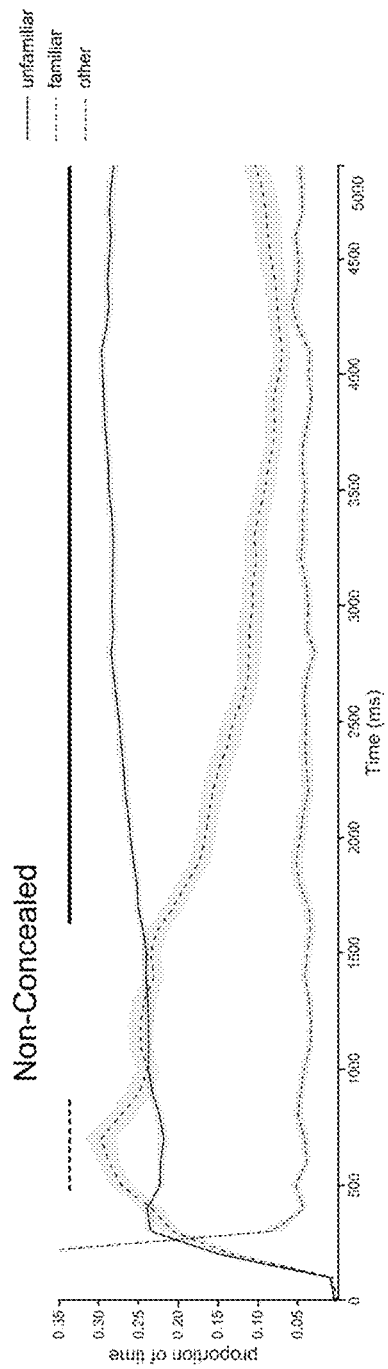
FIGS. 5A, 5B, and 5C show graphs of trials under three different conditions, in accordance with experimental results.
Figure 5B:
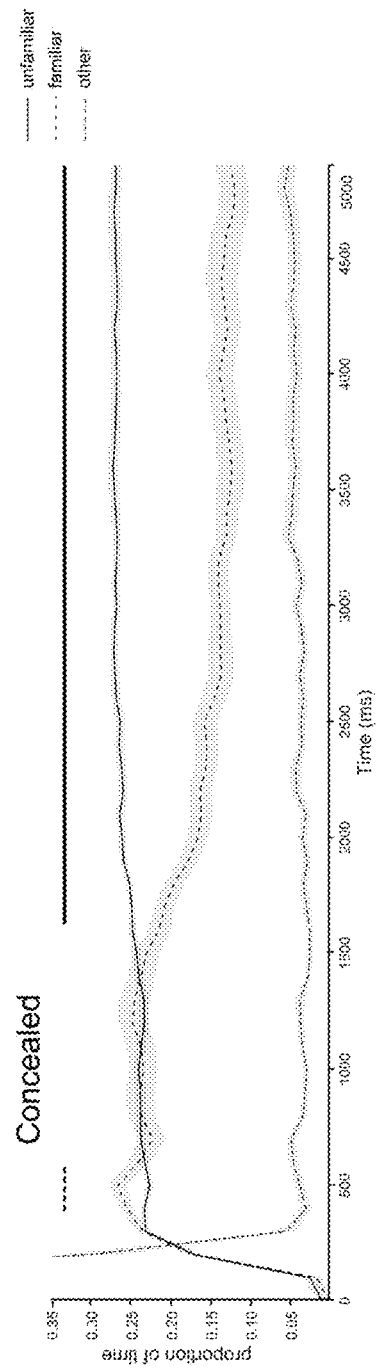
Figure 5C:
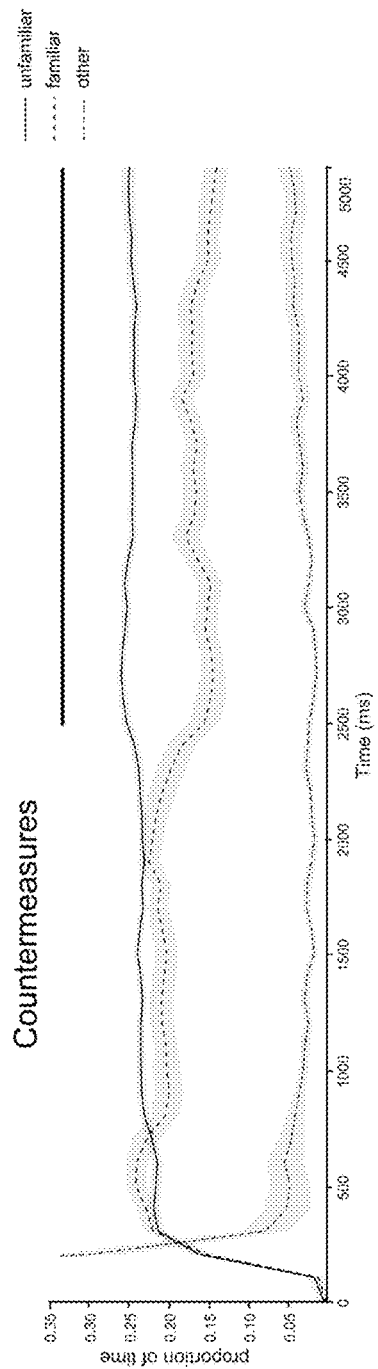

Reference is made to FIGS. 5A, 5B, and 5C showing the experimental results. The purple curves represent proportion of fixating time directed at familiar, the orange curves represent unfamiliar faces (averaged across the 3 unfamiliar faces) during the parallel display. Eye movements outside the interest areas or blinks are represented by the grey curves. Time points with a significant difference (after FDR correction) between familiar and unfamiliar faces are displayed at the top of the figure as purple and orange bars for preference and avoidance effects, respectively. Shadowed area indicates ±1 SE across participants.

In the experiments and analyses, a "visit" was defined as consecutive fixations within the same face area, before a saccade was made outside of that area. On each trial consisting of a familiar face, the number of visits made to the familiar and unfamiliar faces (i.e. the number of times the eyes entered each face area) was calculated.

Figure 6:
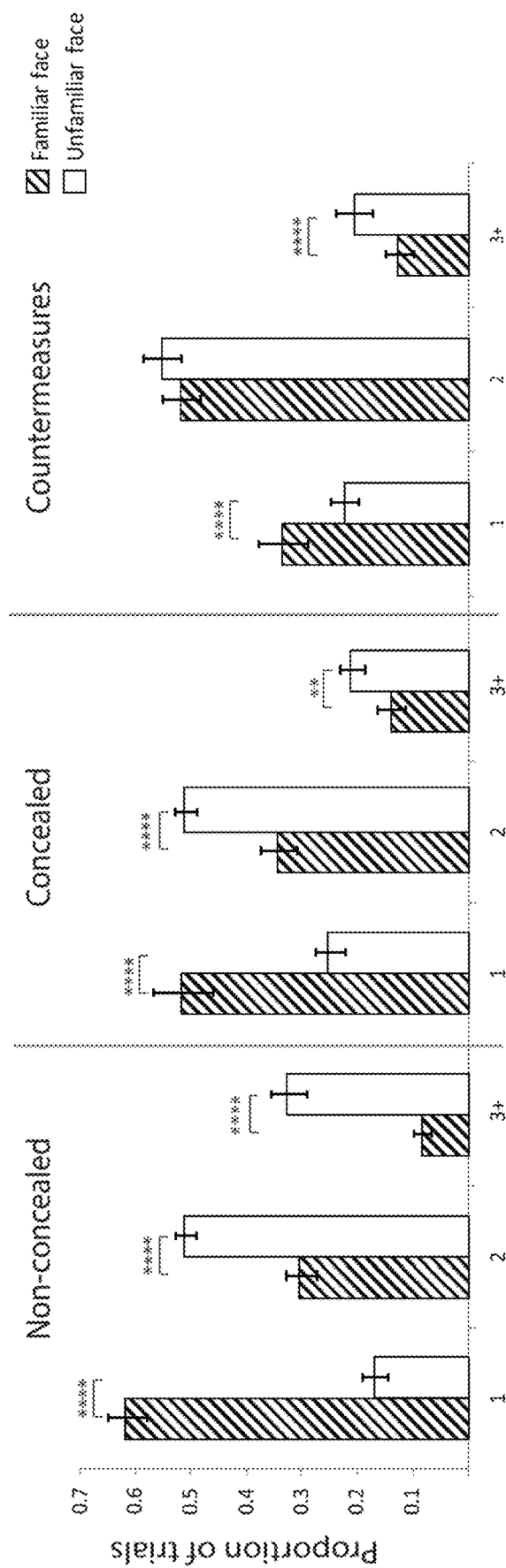
FIG. 6 shows a graph of the proportion of trials in alignment with a number of visits, in accordance with experimental results.

Reference is additionally made to FIG. 6, that illustrates the proportion of trials in alignment with the number of visits. In FIG. 6, proportion of trials with 1, 2 or 3 and more visits to familiar and unfamiliar faces is shown. Distribution of the number of visits (consecutive fixations on a specific face before moving to a different face) in all experiments. Error bars indicate ±1 SE. (P-value<0.01, **P-value<0.001 for paired t-test comparisons between visits to familiar and unfamiliar faces).

Figure 7A:
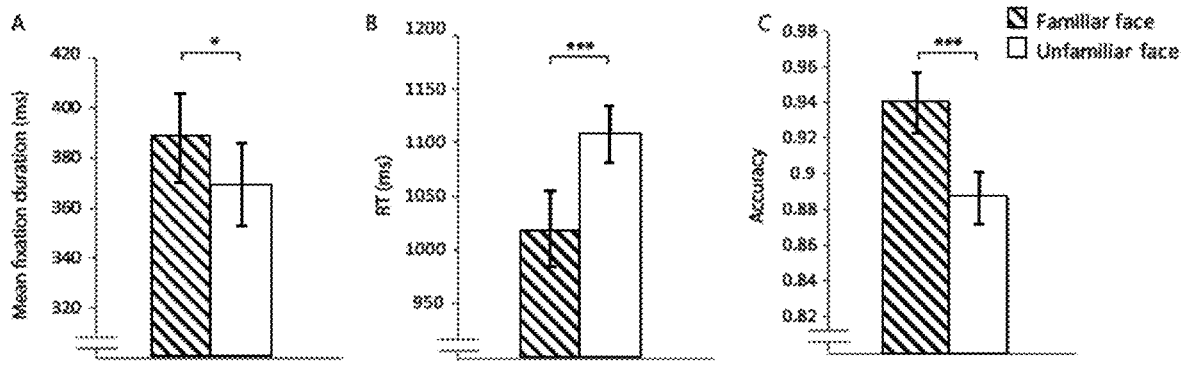
FIGS. 7A, 7B, and 7C show graphs of mean fixation duration during single face display (FIG. 7A), reaction time (FIG. 7B) and accuracy (FIG. 7C) in a short term memory task for familiar and unfamiliar faces, in accordance with experimental results.
Figure 7B:
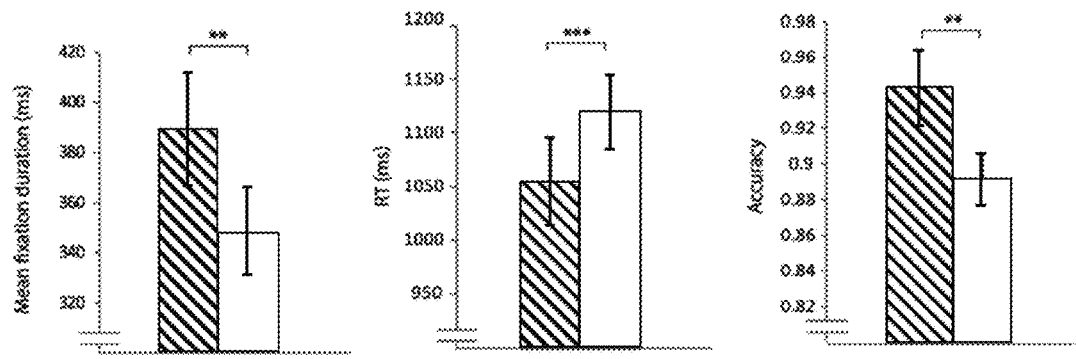
Figure 7C:
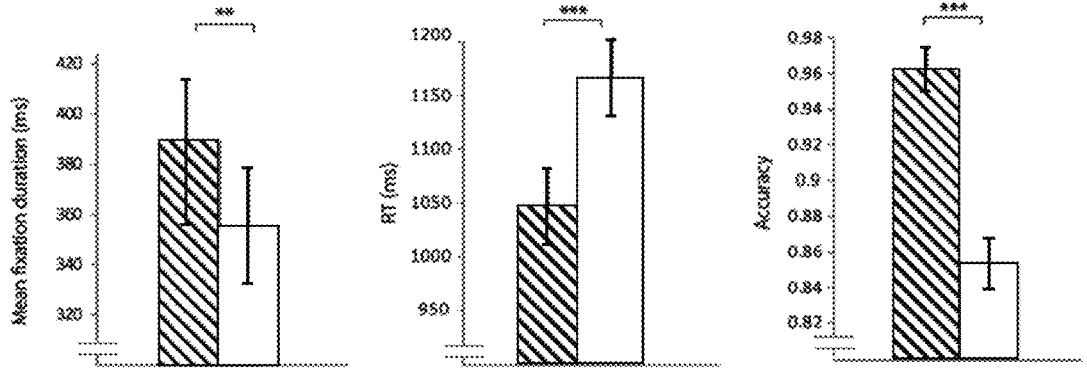

FIGS. 7A, 7B, and 7C present mean fixation duration during single face display (7A), reaction time (7B) and accuracy (7C) in the short term memory task for familiar and unfamiliar faces. Error bars indicate ±SE. (*P-value<0.05, P-value<0.01, *P-value<0.001 for paired t-test comparisons between familiar and unfamiliar faces).

To further examine our main hypothesis (preference for the familiar face during the initial phase followed by avoidance) and compare this pattern across the three experiments, we conducted a three-way ANOVA on the dwell time measures during the parallel display, with two within-subjects factors (familiarity-familiar vs. unfamiliar and dwell time phase-first vs. second) and one between-subjects factor (type of experiment: non-concealed, concealed and countermeasures). In what follows, we report the main effects of interest: (1) the triple interaction between familiarity, dwell time phase and experiment, which reflects the differences in effect sizes in the different experiments, (2) the interaction between familiarity and dwell time phase for each experiment, which reflects the preference and avoidance patterns described above.

The three-way ANOVA revealed a statistically significant triple familiarity*dwell time phase*experiment interaction [$F(2,84)=9.49$, $p<0.001$, $\eta^2_p=0.184$], indicating a different modulation of gaze by familiarity across the three experiments. Furthermore, a familiarity*dwell time phase interaction [$F(1,84)=215.18$, $p<0.001$, $\eta^2_p=0.719$] was found, thus demonstrating a strong effect size of preference and avoidance across the three experiments.

To explore whether the interaction between familiarity and dwell time phase would be found in all experiments we conducted a two-way ANOVA for each experiment with two within-subject factors (familiarity-familiar vs. unfamiliar and dwell time phase-first vs. second). This analysis revealed a significant interaction effect in all experiments: NC [$F(1,28)=168.277$, $p<0.001$, $\eta^2_p=0.857$], C [$F(1,28)=53.488$, $p<0.001$, $\eta^2_p=0.656$] and CM [$F(1,28)=33.258$, $p<0.001$, $\eta^2_p=0.543$]. Thus, whereas each experiment exhibited the expected interaction between familiarity and phase, the triple interaction reflects differences in the sizes of these two-way interactions.

These differences may have important theoretical and practical implications. Specifically, as the sole difference between the experiments is the instructions provided to the participants, directly comparing the concealed and non-concealed experiments would shed light on the effect of concealment effort and the comparison of the concealed and countermeasures experiments would contribute to a better understanding of countermeasures and intentional control of gaze. To that end, we conducted two additional three-way ANOVAs on the dwell time measure during the parallel display. The three factors were familiarity (familiar vs. unfamiliar), dwell time phase (first vs. second) and type of experiment (C vs. NC in the first ANOVA and C vs. CM in the second ANOVA).

For the concealed and non-concealed experiments, the ANOVA revealed a statistically significant two-way interaction between familiarity and dwell time phase [$F(1,56)=188.86$, $p<0.001$, $\eta^2_p=0.771$], indicating an early preference for the familiar faces followed by avoidance in the later phase. A statistically significant triple interaction [$F(1,56)=4.86$, $p=0.032$, $\eta^2_p=0.08$] indicated smaller effect sizes (i.e., interactions between familiarity and phase) in the concealed compared to the non-concealed experiment. The second ANOVA between the concealed and the countermeasures experiments revealed a significant two-way interaction between dwell time and familiarity [$F(1,56)=86.711$, $p<0.001$, $\eta^2_p=0.608$]. The triple interaction was marginally significant [$F(1,56)=3.96$, $p=0.051$, $\eta^2_p=0.066$], with a small effect size.

Receiver Operating Characteristic (ROC) analysis was also made. This analysis revealed high detection efficiency estimates. The areas under the ROC curves in the three experiments were: NC: a=0.976, $p<0.001$ [CI: 0.932,1]; C: a=0.889, $p<0.001$ [CI: 0.800,0.979]; CM: a=0.957, $p<0.001$ [CI: 0.911,1]. These areas are within the highest range of the average areas reported in a recent meta-analysis of traditional concealed information test studies using heart rate, skin conductance response, respiration and event-related brain potentials (i.e. the P300 component). See Meijer, E. H., Selle, N. K., Elber, L., & Ben-Shakhar, G. (2014). Memory detection with the Concealed Information Test: A meta analysis of skin conductance, respiration, heart rate, and P300 data. *Psychophysiology*, 51(9), 879-904.

Importantly, the area in the concealed experiment is comparable to the average areas observed with the most effective physiological measures (SCR–a=0.85; P300–a=0.88) and much higher than the average areas observed with the heart rate (0.74) and respiration (0.77) (Meijer et al., 2014). The difference between the areas under the curve in the concealed and non-concealed experiments was significant (z=1.90, p=0.028), indicating that the effort involved in concealment somewhat degrades detection efficiency. The difference between the areas observed in the concealed and countermeasures experiments was not significant (z=−1.3, p=0.096) but the area difference between the non-concealed and the countermeasure experiments was significant (z=1.69, p=0.045).

SVM—within subject analysis was made, to test the ability to classify pictures as familiar or unfamiliar when training and testing within the same individual. For each participant, the data was separated quasi-randomly into four folds ensuring that all folds contained the same proportion of familiar pictures (2/8). The SVM was trained on three folds of each participant's pictures (48 pictures), and then attempted to classify the remaining fold (16 pictures) as familiar or unfamiliar. This process was iterated four times, each time training and testing on a different combination of the four folds, thus ensuring that each picture would be included once in the test fold. The average classification score for these four iterations within each participant was then aggregated across all participants and compared to chance. The results indicated that 92.2%, 91.3% and 88.7% of the pictures were correctly classified in the non-concealed, concealed and countermeasures experiments, respectively. All these accuracy rates were significantly above chance (NC: t(28)=18.54, p<0.001; C: t(28)=14.63, p<0.001; CM: t(28)=10.05, p<0.001).

SVM—across subjects analysis was made, to evaluate the ability to classify the pictures of each participant as familiar and unfamiliar based on the data of all other participants. For this purpose, the training data consisted of all the participants but one, which enabled us to examine the generalization of gaze behavior after eliminating its idiosyncratic characteristics. This process was iterated 29 times, each time training on the datasets of 28 participants and testing classification accuracy on the data of the remaining participant. Applying this classifier across participants showed average accuracies of 93.4%, 90.8% and 88.7% for the non-concealed, concealed and countermeasures experiments, respectively, again significantly better than chance (NC: t(28)=16.77, p<0.001; C: t(28)=13.77, p<0.001; t(28)=13.72, p<0.001).

All three experiments indicated that when participants encoded multiple faces in parallel, they initially fixated more on the familiar face, followed by a solid tendency to avoid it (see FIGS. 5 and 6). The classification analysis showed that these differences in gaze behavior were robust across individuals, even when participants were told explicitly to conceal their familiarity with their friends and even when they received clear instructions how to do so. The large effect sizes in our experiments and recent advances in eye tracking technology suggest that this paradigm may be implemented successfully to reveal concealed information without direct contact with the examinee outside the lab.

Another finding in the parallel display experiment was that, when the prompt included a familiar face, the participants responded at least 20% more quickly and more accurately to the question whether this face was shown in the previous display. Thus, results of the short-term memory task (both correctness score and a time score) may be harnessed to detect the concealed information.

The subsequent avoidance tendency can be attributed to the short-term memory task. Clearly, the task at hand has crucial influence on the allocation of attention. Because memory plays a central role in this task, an efficient strategy requires looking more at the unfamiliar face during encoding since it is harder to remember. Therefore, the effect we term "avoidance" might reflect a key component of the reciprocal interaction between long-term memory, short-term memory and attention. Our results indicate that a robust representation in long-term memory leads to a more efficient short-term memory encoding process, critically, even when it attracts fewer fixations during encoding.

The current results show that encoding of familiar items in sort-term memory is clearly more efficient since items in long-term memory require less encoding time, but still lead to faster and more accurate memory reports (i.e., responses to the prompt) following brief retention intervals. Regardless of the exact mechanism responsible for the avoidance effect, the introduction of the short-term memory task seems to facilitate differential responses to familiar and unfamiliar items and may help account for the impressive detection efficiency observed in the current study.

What is claimed is:

1. A system comprising:
   a camera;
   a display;
   a controller; and
   a non-transitory computer-readable storage medium having stored thereon instructions that, when executed by said controller:
   operate said display and said camera to administer an eye tracking-based concealed information test to a human subject, and
   administer to the human subject a short-term memory task at least partially in concurrence with the administering of the eye tracking-based concealed information test, to enhance accuracy of the eye tracking-based concealed information test,
   wherein the short-term memory task comprises:
      operating said display to simultaneously present images of objects at certain coordinates on said display;
      operating said camera to track eye movements of the human subject observing said display;
      computing at least one gaze parameter for each of the objects, based on the tracked eye movements and the certain coordinates;
      after said display simultaneously presents images of the objects:
   presenting a prompt that presents one of the images on said display, and
   receiving a response to the prompt from the human subject, wherein the response includes an indication from the human subject as to whether said one of the images appeared in the simultaneous presentation of the images,
   wherein the prompt is textual and/or vocal and wherein the prompt includes instructions to respond to a question or perform a task.

2. The system according to claim 1, wherein the gaze parameter is selected from the group consisting of:
   (a) a total dwell time on each of the objects, wherein the total dwell time is an accumulated time of all gaze fixations during an entire continuous period each of the objects has been presented,
   (b) a partial dwell time on each of the objects, wherein the partial dwell time is an accumulated time of all gaze fixations during a period that begins 0.5-2 seconds after each of the objects has started to be presented,
   (c) a number of visits to each of the objects, and
   (d) a number of fixations on each of the objects; and
   wherein the eye tracking-based concealed information test comprises determining that a certain one of the objects is familiar to the human subject if the gaze parameter has a lower value for the certain one of the objects than for other ones of the objects.

3. The system according to claim 1, wherein the prompt is designed such that the human subject is required to retrieve information from its short-term memory in order to respond to the prompt.

4. The system according to claim 2, wherein the lower value is at least 20% lower.

5. The system according to claim 1, wherein the at least one gaze parameter comprises: (a) the total dwell time on each of the objects, wherein the total dwell time is an accumulated time of all gaze fixations during an entire continuous period each of the objects has been presented, (b) the partial dwell time on each of the objects, wherein the partial dwell time is an accumulated time of all gaze fixations during a period that begins 0.5-2 seconds after each of the objects has started to be presented (c) the number of visits to each of the objects, and (d) the number of fixations on each of the objects.

6. The system according to claim 1, wherein the eye tracking-based concealed information test comprises:
   operating said display to present images of objects, one at a time, at certain coordinates on said display;

operating said camera to track eye movements of the human subject observing said display;

computing at least one gaze parameter for the objects, based on the tracked eye movements and the certain coordinates, wherein the gaze parameter is a mean duration of fixations on the objects;

determining that a certain one of the objects is familiar to the human subject if the gaze parameter has a higher value for the certain one of the objects than for other ones of the objects.

7. A method comprising:

operating a computerized controller to:

administer an eye tracking-based concealed information test to a human subject; and administer to the human subject a short-term memory task at least partially in concurrence with the administering of the eye tracking-based concealed information test, to enhance accuracy of the eye tracking-based concealed information test, wherein the short-term memory task comprises:

operating said display to simultaneously present images of objects at certain coordinates on said display;

operating said camera to track eye movements of the human subject observing said display;

computing at least one gaze parameter for each of the objects, based on the tracked eye movements and the certain coordinates;

after said display simultaneously presents images of the objects:

presenting a prompt that presents one of the images on said display, and receiving a response to the prompt from the human subject, wherein the response includes an indication from the human subject as to whether said one of the images appeared in the simultaneous presentation of the images, wherein the prompt is textual and/or vocal and wherein the prompt includes instructions to respond to a question or perform a task.

8. The method according to claim 7, wherein the gaze parameter is selected from the group consisting of:

(a) a total dwell time on each of the objects, wherein the total dwell time is an accumulated time of all gaze fixations during an entire continuous period each of the objects has been presented, (b) a partial dwell time on each of the objects, wherein the partial dwell time is an accumulated time of all gaze fixations during a period that begins 0.5-2 seconds after each of the objects has started to be presented, (c) a number of visits to each of the objects, and (d) a number of fixations on each of the objects; and wherein the eye tracking-based concealed information test comprises determining that a certain one of the objects is familiar to the human subject if the gaze parameter has a lower value for the certain one of the objects than for other ones of the objects.

9. The method according to claim 8, wherein the lower value is at least 20% lower.

10. The method according to claim 7, wherein the at least one gaze parameter comprises: (a) the total dwell time on each of the objects, wherein the total dwell time is an accumulated time of all gaze fixations during an entire continuous period each of the objects has been presented, (b) the partial dwell time on each of the objects, wherein the partial dwell time is an accumulated time of all gaze fixations during a period that begins 0.5-2 seconds after each of the objects has started to be presented (c) the number of visits to each of the objects, and (d) the number of fixations on each of the objects.

11. The method according to claim 7, wherein the eye tracking-based concealed information test comprises:

operating said display to present images of objects, one at a time, at certain coordinates on said display;

operating said camera to track eye movements of the human subject observing said display;

computing at least one gaze parameter for the objects, based on the tracked eye movements and the certain coordinates, wherein the gaze parameter is a mean duration of fixations on the objects;

determining that a certain one of the objects is familiar to the human subject if the gaze parameter has a higher value for the certain one of the objects than for other ones of the objects.

12. A computer program product comprising a non-transitory computer-readable storage medium having program code embodied therewith, the program code executable by at least one hardware processor to:

administer an eye tracking-based concealed information test to a human subject; and administer to the human subject a short-term memory task at least partially in concurrence with the administering of the eye tracking-based concealed information test, to enhance accuracy of the eye tracking-based concealed information test, wherein the short-term memory task comprises:

operating said display to simultaneously present images of objects at certain coordinates on said display;

operating said camera to track eye movements of the human subject observing said display;

computing at least one gaze parameter for each of the objects, based on the tracked eye movements and the certain coordinates;

after said display simultaneously presents images of the objects:

presenting a prompt that presents one of the images on said display, and receiving a response to the prompt from the human subject, wherein the response includes an indication from the human subject as to whether said one of the images appeared in the simultaneous presentation of the images, wherein the prompt is textual and/or vocal and wherein the prompt includes instructions to respond to a question or perform a task.

13. The computer program product according to claim 12, wherein the program code is further executable by said at least one hardware processor to:

operate a computer display and a camera to administer the eye tracking-based concealed information test; and operate the computer display to administer the short-term memory task.

14. The computer program product according to claim 13, wherein the gaze parameter is selected from the group consisting of:

(a) a total dwell time on each of the objects, wherein the total dwell time is an accumulated time of all gaze fixations during an entire continuous period each of the objects has been presented, (b) a partial dwell time on each of the objects, wherein the partial dwell time is an accumulated time of all gaze fixations during a period that begins 0.5-2 seconds after each of the objects has started to be presented, (c) a number of visits to each of the objects, and
(d) a number of fixations on each of the objects,
wherein the eye tracking-based concealed information test comprises determining that a certain one of the objects is familiar to the human subject if the gaze parameter has a lower value for the certain one of the objects than for other ones of the objects.

15. The computer program product according to claim 14, wherein the lower value is at least 20% lower.

16. The computer program product according to claim 12, wherein the at least one gaze parameter comprises: (a) the total dwell time on each of the objects, wherein the total dwell time is an accumulated time of all gaze fixations during an entire continuous period each of the objects has been presented, (b) the partial dwell time on each of the objects, wherein the partial dwell time is an accumulated time of all gaze fixations during a period that begins 0.5-2 seconds after each of the objects has started to be presented (c) the number of visits to each of the objects and (d) the number of fixations on each of the objects.

17. The computer program product according to claim 12, wherein the eye tracking-based concealed information test comprises:
operating said display to present images of objects, one at a time, at certain coordinates on said display;
operating said camera to track eye movements of the human subject observing said display;
computing at least one gaze parameter for the objects, based on the tracked eye movements and the certain coordinates, wherein the gaze parameter is a mean duration of fixations on the objects;
determining that a certain one of the objects is familiar to the human subject if the gaze parameter has a higher value for the certain one of the objects than for other ones of the objects.

* * * * *

UNITED STATES PATENT AND TRADEMARK OFFICE
CERTIFICATE OF CORRECTION

| | | |
|---|---|---|
| PATENT NO. | : 11,020,034 B2 | |
| APPLICATION NO. | : 16/612420 | |
| DATED | : June 1, 2021 | |
| INVENTOR(S) | : Pertzov et al. | |

It is certified that error appears in the above-identified patent and that said Letters Patent is hereby corrected as shown below:

On the Title Page

Please correct item (73) the assignee name to: YISSUM RESEARCH DEVELOPMENT COMPANY OF THE HEBREW UNIVERSITY OF JERUSALEM LTD.

Signed and Sealed this
Eleventh Day of October, 2022

Katherine Kelly Vidal
*Director of the United States Patent and Trademark Office*